United States Patent
Richardson

(10) Patent No.: US 6,623,466 B1
(45) Date of Patent: Sep. 23, 2003

(54) ABSORBENT ARTICLE HAVING DETACHABLE COMPONENTS

(76) Inventor: Irene Richardson, 19027 Armington Dr., El Paso, TX (US) 79927

(*) Notice: Subject to any disclaimer, the term of this patent is extended or adjusted under 35 U.S.C. 154(b) by 77 days.

(21) Appl. No.: 09/175,100

(22) Filed: Oct. 19, 1998

Related U.S. Application Data

(60) Provisional application No. 60/062,757, filed on Oct. 23, 1997.

(51) Int. Cl.$^7$ ................................................ A61F 13/15
(52) U.S. Cl. ............................ 604/385.19; 604/385.13; 604/385.14; 604/385.11
(58) Field of Search ........................ 604/385.14, 385.11, 604/385.19, 385.23, 385.01, 395, 378, 385.13, 393, 397, 402, 364

(56) References Cited

U.S. PATENT DOCUMENTS

| | | | | |
|---|---|---|---|---|
| 3,842,838 A | | 10/1974 | Gellert ........................ 128/284 |
| 3,860,003 A | | 1/1975 | Buell .......................... 128/287 |
| 3,882,871 A | * | 5/1975 | Taniguchi ..................... 128/287 |
| 4,515,595 A | | 5/1985 | Kievit et al. ............ 604/385 A |
| 4,597,760 A | * | 7/1986 | Buell .......................... 604/397 |
| 4,834,737 A | * | 5/1989 | Khan ....................... 604/385.2 |
| 4,892,598 A | | 1/1990 | Stevens et al. ................. 156/91 |
| 4,964,857 A | | 10/1990 | Osborn ........................ 604/395 |
| 5,069,672 A | | 12/1991 | Wippler et al. ........... 604/385.1 |
| 5,071,414 A | | 12/1991 | Elliott ...................... 604/385.1 |
| 5,207,665 A | * | 5/1993 | Davis et al. ................. 604/399 |
| 5,217,447 A | * | 6/1993 | Gagnon ........................ 604/397 |
| 5,325,543 A | * | 7/1994 | Allen ............................ 2/406 |
| 5,342,340 A | | 8/1994 | Kichetski et al. ......... 604/385.1 |
| 5,360,422 A | | 11/1994 | Brownlee et al. ......... 604/385.2 |
| 5,368,585 A | | 11/1994 | Dokken ....................... 604/393 |
| 5,405,342 A | * | 4/1995 | Roessler et al. ............ 604/364 |
| 5,409,476 A | | 4/1995 | Coates ........................ 604/391 |
| 5,476,457 A | | 12/1995 | Roessler et al. ............ 604/364 |
| 5,575,784 A | | 11/1996 | Ames-Ooten et al. ... 604/385.1 |
| 5,613,959 A | | 3/1997 | Roessler et al. ............ 604/364 |
| 5,667,503 A | | 9/1997 | Roe et al. ................ 604/385.1 |

* cited by examiner

Primary Examiner—Weilun Lo
Assistant Examiner—Jacqueline F Stephens
(74) Attorney, Agent, or Firm—Henry L. Smith, Jr.

(57) ABSTRACT

An absorbent article including a disposable diaper, reusable diaper, feminine care pad, training pants, incontinence garment and the like. The article comprises a detachable flushable topsheet and an absorbent pouch containing absorbent contents; however, the detachable topsheet is optional. A fastening means releasably attaches the absorbent pouch in a stationary position within the article and prevents the pouch from shifting with respect to the article. The detachable topsheet can be removed from the article and flushed in a toilet together with the human waste. A binding allows the pouch to be opened to flush the absorbent contents and human waste inside the pouch, in segments to avoid clogging a toilet. Instead of flushing, the absorbent pouch can be removed from the article and disposed of in a waste receptacle, by rolling the pouch, with minimum finger contact with human waste, and securing the pouch to itself using an adhesive tab.

31 Claims, 10 Drawing Sheets

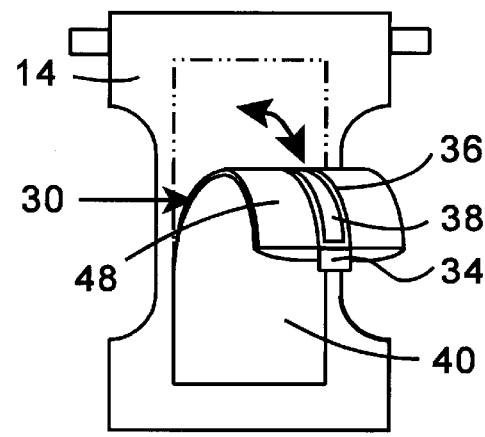
FIG. 5
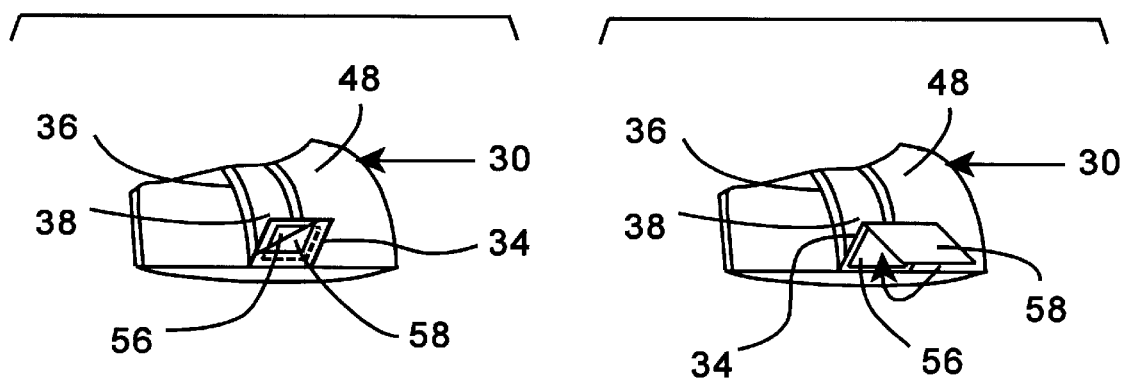
FIG. 5A
FIG. 5B

ABSORBENT ARTICLE HAVING DETACHABLE COMPONENTS

The invention was the subject of a Provisional Patent Application #60/062,757 filed Oct. 23, 1997.

FIELD OF THE INVENTION

The present invention pertains to an absorbent article, such as a diaper, feminine care pad, incontinence garment, training pants and the like. More particularly, the present invention relates to an absorbent article with an improved design which allows portions of the article to become detached in various predetermined locations.

BACKGROUND OF THE INVENTION

The main function of absorbent articles such as diapers, adult incontinence garments, feminine care pads and training pants is to absorb and contain body exudates. Such articles are thus placed against or in proximity to the body of the wearer to absorb and contain the various exudates discharged from the body. Contemporary disposable absorbent articles are permanently unitary and are intended to be discarded after a single use. Articles such as disposable diapers are generally comprised of a liquid permeable topsheet, a liquid impermeable backsheet, an absorbent core, elasticized leg flaps, and tape tabs.

The most common mode of failure for such products is the negative environmental repercussions which predominantly result after disposing of the used article. Presently, used absorbent articles are rolled and secured with the article's adhesive fastening means, thus permanently enclosing the article and its contents within the confines of the liquid impermeable backsheet. The article is then discarded, solid-waste and all, and is finally delivered to a landfill where it may remain for centuries until it degrades. These two factors are the primary contributors to the environmental stigma associated with absorbent articles, in particular disposable diapers. Contemporary disposable diapers do not provide a sanitary means for the disposal of fecal material, such as by flushing the material down the toilet where it can be treated by the sewage system. Manufacturers of these articles have not provided a suitable solution to this environmental problem, but have merely printed instructions on the packaging asking the consumer to shake the diaper over the toilet to remove the solid waste material before discarding. The other environmental hazard associated with disposable diapers, is the impact they have had on landfills. Although some contemporary disposable diapers are made with bio-degradable material, the greatest problem stems from the liquid impermeable material of the backsheet which is non-biodegradable and, consequently, inhibits the breakdown of the diaper when thrown away. The problem is primarily due to the above-mentioned process of wrapping the used diaper with the backsheet, prior to discarding. This process completely and permanently traps the biodegradable material and the waste within the non-biodegradable material prior to sending the used article to the landfill. The problem is amplified since each child wears about 6000 disposable diapers before being toilet-trained, which amounts to approximately 16 billion diapers being discarded annually in the U.S. These figures explain why this single product, used by a steadily increasing group of the population, accounts for approximately 2% of landfill capacity.

An alternative, such as the disposable diaper with flushable components as the one disclosed in U.S. Pat. No. 5,476,457 and U.S. Pat. No. 5,405,342 issued to Roessler et al. on Dec. 19, 1995 and Apr. 11, 1995 respectively, includes a diaper with a flushable insert pad. The entire insert pad is dropped into the toilet, where it must remain for at least two minutes prior to flushing. This method suffers from the disadvantages of imposing this waiting period on the consumer before flushing, potentially causing the toilet to clog due to the compact structure of the insert pad and from flushing the insert pad as a whole into the toilet, and shifting of the insert pad, due to the absence of a mechanism to secure the insert pad to the absorbent article. The only mechanism used to maintain the insert pad in position within the diaper is the cover that is placed over the insert pad; however, the cover does not keep the insert pad from moving inside the diaper. Therefore, once the insert pad has been wetted, the insert pad is free to move inside the diaper, which may clump to the center of the diaper. The clumping of the absorbent material to the center of the diaper, may compromise the absorbent capacity of the article by the non-uniform dispersement of the absorbent material and may also result in discomfort to the wearer from the clumping of the absorbent material in the center of the diaper. As mentioned above, the other disadvantage of the design is the problem that results from the construction of the insert pad being designed to be flushed as a whole in that the flushable design is limited to smaller size diapers, due to the fact that larger diapers with larger insert pads would clog the toilet when flushed. However, the above disadvantages have not been confirmed, since the articles of the prior-art are not available on the market.

As a result of the environmental drawbacks associated with disposable diapers, reusable absorbent articles have become a popular alternative for consumers. New customized designs, resembling disposable diapers, have been incorporated into the design of reusable retainers such as the one disclosed in U.S. Pat. No. 5,409,476 issued to Fredrica Coates on Apr. 25, 1995. These reusable retainers are used in conjunction with cloth diapers, but are also used with disposable absorbent insert pads. This alternative suffers from a number of disadvantages. For instance, reusable absorbent articles leak more, do not keep the wearers as dry as disposable diapers, are more time consuming to use and wash, require much more maintenance, are less sanitary, are less reliable, and damage the ecology by creating waste water.

Conventional absorbent articles, such as those described above, have not been completely satisfactory in providing a suitable solution to the ecological problem. Therefore, a simple, effective and reliable process for disposing of these articles is needed which also promotes the preservation of the environment. Nevertheless, the only absorbent articles available suffer from a number of disadvantages.

Therefore, it is an object of the present invention to provide an absorbent article having an improved design, which temporarily joins various significant components of the article in an unconventional manner.

It is another object of the present invention to provide an improved design for absorbent articles which allows for the separation of these significant components of the article in order to discard them separately in a more sanitary and environmentally friendly manner.

It is also an object of the present invention to provide an absorbent article having a biodegradable detachable liner which can be flushed down the sewage system separately, and thus removing most of the solid waste material contained on the absorbent article, prior to discarding it.

It is further an object of the present invention to provide an improved design for an absorbent article having a pulling means to grip the detachable liner to tear it away from the topsheet of the article.

It is an object of the present invention to provide an absorbent article having an absorbent pouch, which encloses all the absorbent contents of the article located between the topsheet and backsheet.

It is another object of the present invention to provide an improved design for an absorbent article, which allows for the detachment of the absorbent pouch binding in order to expose and release its absorbent contents.

It is an additional object of the present invention to provide an absorbent article having a means of releasably attaching the absorbent pouch to the article, which means can also be utilized to detach the pouch prior to discarding.

It is also an object of the present invention to provide an improved design for an absorbent article which allows for the extraction of the absorbent pouch through the opening created after removing the detachable liner, and which consequently allows for the pouch to be discarded separately from the article.

It is another object of the present invention to provide an absorbent article having a means of gripping the absorbent pouch to remove it from the article, and also having a means which allows for the handling and securing of the pouch with minimal finger contact with the human wastes, prior to discarding.

Furthermore, it is also an object of the present invention to provide an absorbent article having an absorbent pouch which can be used alone, independent of other components of the article. It is an object of the present invention to provide a process of making the absorbent article.

Finally, it is an object of the present invention to provide an absorbent article which allows the user the convenient option of disposing the detachable components at a landfill site or in a toilet, thereby accommodating the preference of the individual and the capability of the community.

Other objects and advantages of the present invention will become readily apparent to those skilled in the art from the following detailed description, wherein the preferred embodiment of the invention is shown and described, simply by way of illustration of the best mode contemplated of carrying out the invention.

BRIEF DESCRIPTION OF THE INVENTION

In accordance with one aspect of the invention, there is provided an improvement for a disposable absorbent article, such as a diaper, adult incontinence garment, feminine care pad, and training pants, having various detachable components. These components are temporarily joined but have a means of detaching these components from the article after use and disposing of them separately. The present invention is an improvement that can be implemented and utilized to supplement contemporary disposable absorbent articles. Present commercially available disposable diapers comprise a liquid permeable topsheet, an absorbent core, a liquid impermeable backsheet, tape tabs, leg elastic members and waist elastic members. The improvement of the present invention comprises elements described below, which make up the preferred embodiment. A liquid permeable topsheet and a liquid impermeable backsheet are bound together in facing relation, thus creating a hollow containment pocket, which encases an inner liquid permeable absorbent pouch. The absorbent pouch has a releasable binding along the entire periphery of the absorbent pouch to encase the absorbent contents of the absorbent article located within the hollow containment pocket. However, the releasable binding is used to encase all the absorbent contents of the article within the absorbent pouch, and not for holding the absorbent pouch to the absorbent article, nor within the hollow containment pocket. An alteration is applied to the topsheet by adding a detaching means to its surface, thus providing a means for removing a substantial portion of the topsheet, which is referred to as a detachable liner. The detachable liner can be extracted from the surface of the topsheet by taking hold of pulling tabs, located on the top and bottom peaks of the detachable liner, and continuing to pull along the periphery of the detaching means until the entire detachable liner has been completely removed from the topsheet; Once the detachable liner has been extracted from the absorbent article, it can be flushed down the toilet, along with any accompanying body exudates contained on the liner. An opening is thus created on the outer surface of the topsheet, after the detachable liner has been completely removed, to release the absorbent pouch from the interior of the absorbent article. A gripping tab is used to pull the absorbent pouch and extract it through the opening to release the pouch from the confines of the absorbent article. The absorbent pouch is releasably secured to the backsheet of the absorbent article by a securement strip and a fastening means to prevent the pouch from shifting out of position. As used in this Application, the term fastening means refers to an element which connects the pouch to the framework of the article itself, and is distinct from the detachable liner, which covers the pouch but does not positively attach the pouch to the frame work of the article. The fastening means prevents the pouch from moving with respect to the framework of the article; the detachable liner covering the pouch does not provide that function, and in other art which lacks a fastening means, the pouch can move under the detachable liner and thus change position with respect to the framework of the article. The absorbent pouch is secured to the backsheet until it is extracted out of the opening to be discarded separately after use. Prior to being discarded, the absorbent pouch is rolled into its final position and permanently secured by fastening the gripping tab to the fastening means.. After the absorbent pouch has been prepared for disposal, it can be discarded separately from the remnants of the absorbent article. The absorbent pouch, which contains the majority of the article's absorbent material, has a higher potential for biodegrading now because it is no longer attached to the backsheet, which inhibits decomposition of the article after being thrown away. A preferred alternative for the disposal of the absorbent pouch is to flush the absorbent contents down a toilet. This is performed by taking hold of peeling tabs located on the top edge of absorbent pouch and pulling until the releasable binding breaks and separates the outer protective layers of the absorbent pouch to expose the flushable absorbent contents of the absorbent pouch and allow them to fall by gravity into the toilet. Depending on the size of the article and the flushing capacity of the toilet, the user may also flush the contents of the absorbent pouch in segments to reduce the risk of clogging the toilet. The releasable binding of the absorbent pouch allows for the pouch to be opened and for the disposal of the absorbent contents to be regulated by the, user, and therefore, larger size articles can be flushed in segments without clogging the toilet. The absorbent pouch, as a whole, is not intended to be flushed, rather it is designed to become detached and only the absorbent contents of the pouch are flushable. Therefore, the applications of the detachable design of the absorbent article are more diverse, and therefore, adapted to be used with larger size articles and with a wider spectrum of disposable hygienic articles. In an alternative embodiment of the absorbent pouch, the pouch is used alone, independent of the hollow containment pocket and the detachable liner, and is fastened to reusable undergarments, diaper covers, training pants, or other similar reusable garments.

The detachable structure of the absorbent article provides various alternatives to individually discard each component. The improved design is potentially advantageous to the preservation of the ecology by providing a variety of unconventional and more suitable methods of discarding disposable absorbent articles. Variations in the operation and utilization of the invention are applicable, and the above mentioned embodiments are only examples and not limitations. As will be realized, the invention is capable of other and different embodiments, and its several details are capable of modifications in various obvious respects, all without departing from the scope of the invention. Accordingly, the drawings and descriptions are to be regarded as illustrative in nature, and not as restrictive.

BRIEF DESCRIPTION OF THE DRAWINGS

The invention will be more fully understood and further advantages will become apparent when reference is made to the following detailed description of the invention and the following drawings in which:

FIG. 5 representatively shows a perspective view of the absorbent article having moving parts to illustrate the improvements of the present invention.

FIG. 5A representatively shows a perspective view of a portion of the absorbent pouch having moving parts to illustrate the improvements of the present invention.

FIG. 5B representatively shows a perspective view of a preferred embodiment of a portion of the absorbent pouch having moving parts to illustrate the functionality of the present invention.

REFERENCE NUMERALS IN DRAWINGS

Figure 1:
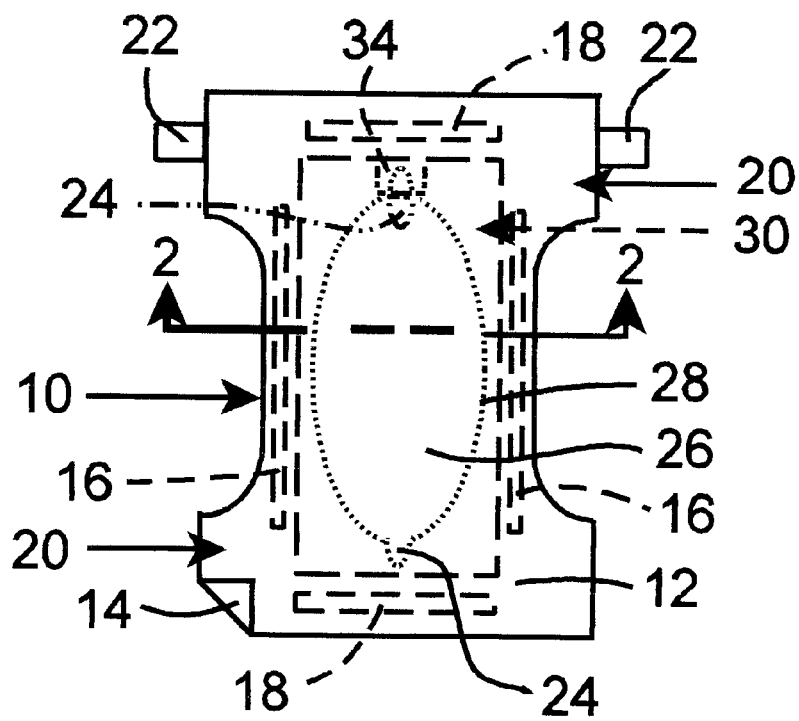
FIG. 1 representatively shows a top plan view of the absorbent article in a stretched condition having hidden lines and portions folded back to clearly show the interior construction.

| | |
|---|---|
| 10 | disposable diaper article |
| 12 | liquid permeable topsheet |
| 14 | liquid impermeable backsheet |
| 16 | leg elastic members |
| 18 | waist elastic members |
| 20 | I-shape plan form |
| 22 | diaper fastening members |
| 24 | pulling tab for detachable liner |
| 26 | detachable liner |
| 28 | detaching means for liner |
| 30 | absorbent pouch |
| 32 | opening |
| 34 | gripping tab for absorbent pouch |
| 36 | securement strip for absorbent pouch |
| 38 | fastening means for absorbent pouch |
| 40 | liquid permeable top layer |
| 42 | top tissue layer |
| 44 | absorbent body |
| 46 | bottom tissue layer |
| 48 | liquid permeable bottom layer |
| 50 | absorbent pouch rectangular shape |
| 52 | top and bottom binding |
| 54 | lengthwise binding |
| 56 | tab adhesive |
| 58 | release liner |
| 60 | barrier cuffs |
| 62 | solid waste |
| 64 | peeling tabs for absorbent pouch |
| 66 | hollow containment pocket |
| 68 | waste receptacle |
| 70 | toilet |
| 72 | reusable diaper cover |

SUMMARY OF THE INVENTION

The invention is a disposable absorbent article, such as a diaper, which, in one of its preferred embodiments, has a hollow pocket releasably containing an absorbent pouch which can release its contents for flushing, and which has a detachable liner in contact with the wearer. The invention also includes the process of making the absorbent article.

DETAILED DESCRIPTION OF THE INVENTION

The following detailed description will be made in the context of a disposable diaper article. It is readily apparent, however, that the absorbent structure of the present invention would also be suitable for other absorbent articles, such as feminine care pads, incontinence garments, training pants, reusable diapers, and the like.

The present invention is an improvement which can be implemented into the design of contemporary disposable absorbent articles, such as those disclosed in U.S. Pat. No. 3,860,003 issued to Kenneth Barclay Buell on Jan. 14, 1975 and in U.S. Pat. No. 4,515,595 issued to D. J. Kievet and T. F. Osterhage on May 7, 1985. In order to describe and incorporate the improvements of the present invention, thoroughly, it will be necessary to refer to prior art elements of contemporary disposable absorbent articles such as those illustrated in FIG. 1. A conventional absorbent article, such as disposable diaper 10, comprises a substantially liquid permeable absorbent core sandwiched between a liquid permeable topsheet layer 12 and a liquid impermeable backsheet 14. Diaper 10 has a generally I-shape plan form 20 with fastening members 22 for fastening the diaper 10 on the wearer. The illustrated embodiment further includes leg elastic members 16 configured to gather and shirr the leg band portions of diaper 10 to form seals or gaskets about the legs of the wearer. In addition, diaper 10 includes waist elastic members 18 to gather and shirr the waistband portions of the diaper 10 to form seals or gaskets about the waist of the wearer. These above-mentioned elements of prior art are not features of the present invention, but are only referenced for clarity of the present invention. Although tape tabs 22 are not elements of the present invention, they will be included in several of the drawings to depict the orientation of the absorbent article. Furthermore, the elements of the present invention are improvements that can be added and combined with the design of contemporary absorbent articles in order to supplement and enhance the prior art.

Topsheet 12 is compliant, soft feeling, and nonirritating to the wearer's skin. Further, the topsheet 12 is liquid pervious permitting liquids to readily penetrate through its thickness. Typically, topsheet 12 is composed of a liquid permeable hydrophobic fibrous material that is well known in the art, such as a spunbonded web composed of synthetic polymer filaments, to isolate the wearer's skin from liquids in the absorbent core. A suitable topsheet 12 may be manufactured from a wide range of materials, such as natural fibers, synthetic fibers, or a combination of natural and synthetic fibers. Alternatively, topsheet 12 may comprise a meltblown web or a bonded-carded-web composed of synthetic polymer filaments, such as polyethylene, polypropylene, and polyesters, or a web of natural polymer filaments, such as cotton or rayon. Flushable material is used to manufacture topsheet 12. Furthermore, topsheet biodegradable material which is susceptible to breakdown over a relatively short period of time, when exposed to natural elements such as air, heat and moisture, can be used to accelerate the degrading process once discarded. Topsheet 12 is substantially noncoterminous with the backsheet 14 so that liquids will not wick through the topsheet 12, thereby reducing the leakage of liquids out of the diaper 10. The topsheet 12 is positioned adjacent the body surface of an absorbent core and overlays a major portion of the absorbent core so that liquid exudates are discharged onto the topsheet 12 and penetrate through the topsheet 12 where they are absorbed by the absorbent core. The topsheet 12 extends outwardly toward the edges of the absorbent core so that a major portion of the absorbent core is contained between the backsheet 14 and the topsheet 12. In the preferred embodiment shown in FIG. 1, the topsheet 12 has length and width dimensions generally larger than those of the absorbent core.

Backsheet 14 is impervious to liquids and is preferably manufactured from a thin plastic film, although other flexible liquid impervious materials may also be used. As used herein, the term flexible refers to materials which are compliant and which will readily conform to the general shape and contours of the human body. The backsheet 14 prevents the exudates absorbed and contained in the absorbent core from wetting articles which contact the diaper 10, such as bed sheets and undergarments. Backsheet 14 can be composed of a polyolefin film, such as polyethylene or polypropylene. Further, backsheet 14 may be composed of a vapor permeable material such as a breathable, microporous polyethylene film. In another embodiment, backsheet 14 can also be composed of a liquid impermeable, but vapor permeable, nonwoven fibrous material, which has been suitably treated to impart a desired degree of liquid impermeability. For example, backsheet 14 may be composed of a nonwoven spunbonded layer, which has been completely or partially coated with a polymer film to provide liquid impermeability in particular areas. The size of the backsheet 14 is dictated by the size of absorbent core and the exact diaper design selected. In a preferred embodiment, both topsheet 12 and backsheet 14 have an I-shape plan form 20 extending beyond the absorbent core, but backsheet 14 is slightly larger in proportion and surpasses the periphery of topsheet 12. Topsheet 12 and backsheet 14 are bound along the edges of the I-shape plan 20 form so as to form a leakage-resistant seal along the entire perimeter of diaper 10.

Various components of diaper 10 are assembled employing conventional techniques such as those well known in the art. Components may be attached by employing thermal bonding or attached with adhesives, such as hot melt pressure-sensitive adhesives.

Figure 2:
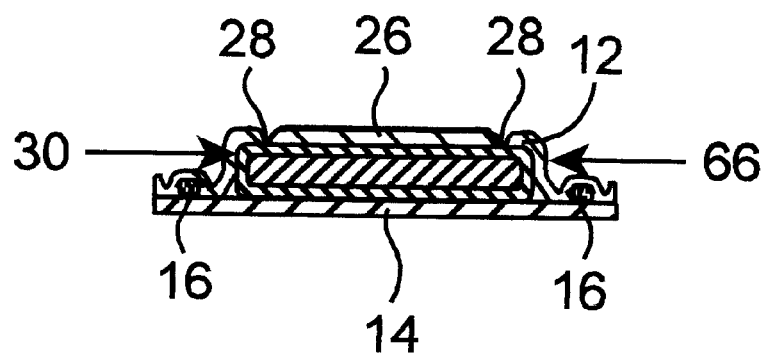
FIG. 2 representatively shows a cross-sectional view of the absorbent article taken along line 2—2 of FIG. 1 of the present invention. Full details of the pouch and securement strip, etc. are shown in FIG. 7.

The following descriptions will be in reference to the novel elements of the present invention. As illustrated in FIGS. 1 and 2, an alteration is applied to topsheet 12 by adding a detaching means 28 and pulling tabs 24 to the surface of topsheet 12, thus, improving the function of diaper 10 by allowing a detachable liner 26 to be extracted from the surface of topsheet 12. The previously-mentioned absorbent core will now be referred to as an inner liquid-permeable absorbent pouch 30. In the embodiment illustrated in FIG. 2, topsheet 12 and backsheet 14 are bound together in a facing relation, thus creating a hollow containment pocket 66 which encases the absorbent pouch 30 as shown in FIG. 2. As shown on FIG. 7, absorbent pouch 30 is releasably bound to enclose the absorbent contents 42, 44, 46, in facing relation to its top and bottom surfaces, which comprise a liquid permeable top layer 40, a top tissue layer 42, an absorbent body 44, a bottom tissue layer 46, and a liquid permeable bottom layer 48. As shown in FIGS. 1 and 2, topsheet 12 and backsheet 14 extend out past the edges of absorbent pouch 30.

Figure 3:
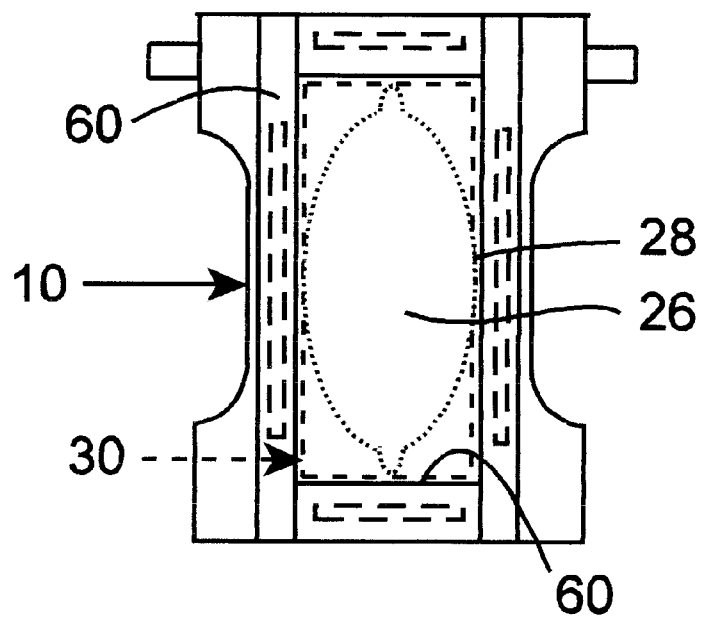
FIG. 3 representatively shows a top plan view of a typical prior art absorbent article in a stretched condition with improvements of the present invention added.

The embodiment shown in FIG. 3 depicts another configuration of a contemporary prior art absorbent article used in conjunction with the improvements of the present invention. FIG. 3 includes all the elements previously described in FIG. 1, with the addition of barrier cuffs 60 as described in U.S. Pat. No. 4,938,755 issued to John H. Foreman on Jul. 3, 1990. Although the barrier cuffs are not elements of the present invention, they are referenced to identify significant boundaries in which detachable liner 26 and absorbent pouch 30 should be confined within as illustrated in FIGS. 1 and 3. In order for detachable liner 26 and absorbent pouch 30 to function properly, they should not exceed the boundary designated by the position of the leg elastic members 16 and the waist elastic members 18 as depicted in FIG. 1. As shown in FIG. 3, the detachable liner 26 must not surpass the perimeter designated on the surface of topsheet 12 where the barrier cuffs 60 are positioned and come in contact with topsheet 12. Therefore, the dimensions of detachable liner 26 and absorbent pouch 30 are dictated by the locations and peripheries of leg elastic members 16, waist elastic members 18, and barrier cuffs 60.

Figure 4:
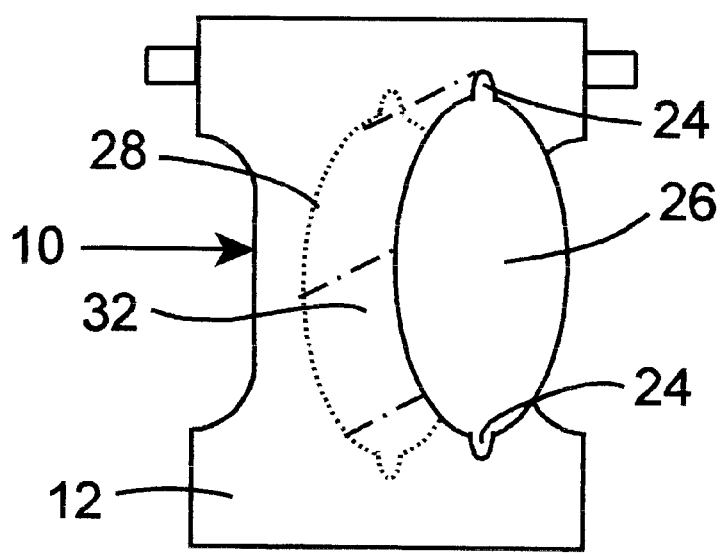
FIG. 4 representatively shows an exploded view of the absorbent article illustrating improvements of the present invention.

FIG. 4 illustrates the detachable liner 26 and those elements used in its construction and utilization. In the preferred embodiment, pulling tabs 24 and detaching means 28 are alterations incorporated onto the surface of topsheet 12, and thus construct the detachable liner 26. Detaching means 28 encompasses the entire periphery of the detachable liner 26 and pulling tab 24. Preferably, pulling tabs 24 and detaching means 28 are an integral portion of topsheet 12 and are utilized to provide a means of tearing the detachable liner 26 off from topsheet 12. The extraction of detachable liner 26, consequently, creates an opening 32 on the surface of the topsheet 12 which is utilized to release the absorbent pouch 30 from the confines of the diaper 10. As displayed in FIG. 4, the size, shape and configuration of detaching means 28 establishes the periphery of both detachable liner 26 and opening 32.

In the preferred embodiment, detaching means 28 can be manufactured by making a series of perforations along the surface of topsheet 12 throughout the entire periphery of detachable liner 26. Other detaching means can be used to produce similar results. In the illustrated embodiment, detachable liner 26 is shown to have an elliptically-shaped outline and includes pulling tabs 24 on the top and bottom peaks of the liner. Many variations in size, shape, and location can be incorporated for the design of detaching means 28. For example, detaching means 28 can be rectangular and incorporate the entire area of topsheet 12 between barrier cuffs 60 and elastic waist members 18.

Pulling tabs 24 are added to detaching means 28 and detachable liner 26 in order to provide a means of gripping and pulling on detaching means 28 to facilitate in extracting detachable liner 26. Pulling tabs 24 are preferably finger-sized and have a rounded shape sufficient to provide a means of gripping detachable liner 26 to tear it away from topsheet 12 with the optimum level of ease and convenience to the user. In the preferred embodiment, pulling tabs 24 are shown as integral extensions of detachable liner 26. The options for the location of pulling tabs 24 on the detachable liner 26 include: the central upper peak, the central lower peak, both upper and lower peaks, or they may be omitted altogether. In the preferred embodiment, pulling tabs 24 incorporate the upper and lower peak portions of detachable liner 26 and, therefore, are composed of the same material used for the topsheet 12. It is readily apparent that pulling tabs 24 do not necessarily have to embody the same surface as detachable liner 26 and can be made of a different material from the detachable liner 26 and topsheet 12. In the illustrated embodiment, the shape of pulling tabs 24 is convex; although, it is readily apparent that other shapes, such as parabolic, triangular, or rectangular may also be used. Variations of sufficient size, shape and configuration of pulling tabs 24 can be employed for optimum efficiency.

FIG. 5 displays the absorbent pouch 30 in two positions along backsheet 14. In one position, a portion of the absorbent pouch 30 is shown superposed in facing relation with backsheet 14. In the other position, a portion of the absorbent pouch 30 is displayed folded away from the backsheet 14, and thus revealing the surface of the absorbent pouch 30 that is in contact relation to backsheet 14. Absorbent pouch 30 is positioned along the lateral and lengthwise center lines of backsheet 14. Securement strip 36 and fastening means 38 releasably join the absorbent pouch 30 to backsheet 14. Fastening means 38 secures absorbent pouch 30 into position and prevents it from shifting or moving out of place with respect to the body 10 of the absorbent article. Securement strip 36 is shown positioned along the lengthwise center line of absorbent pouch 30. Gripping tab 34 is shown as an integral extension of securement strip 36, which surpasses the length of absorbent pouch 30 beyond the top edge. In the preferred embodiment, gripping tab 34 is located on the top edge of absorbent pouch 30, which is on the same end of backsheet 14 where fastening members 22 are found. It is readily apparent that the gripping tab 34 can also be oriented on the opposite end of absorbent pouch 30 or on both ends of absorbent pouch 30.

Securement strip 36 is utilized for multiple functions. First, used in conjunction with fastening means 38, securement strip 36 is used to releasably join absorbent pouch 30 with backsheet 14 to secure absorbent pouch 30 into position and prevent it from shifting or moving out of place in diaper 10. In addition, securement strip 36 is used to handle the absorbent pouch 30 after use, to prevent direct contact by fingers with the wet surface while preparing the absorbent pouch 30 for disposal. Furthermore, securement strip 36 is used to permanently secure the absorbent pouch 30 into its final rolled position prior to discarding, by fastening gripping tab 34 to the fastening means 38. Securement strip 36 is composed of a liquid impermeable material that is well known in the art, such as the same material used for backsheet 14. Securement strip 36 is sandwiched between bottom layer 48 and backsheet 14. In the preferred embodiment, the length of securement strip 36 extends beyond the length of absorbent pouch 30. The width of securement strip 36 can be varied depending on the size of the absorbent pouch 30. In the embodiment of FIG. 5, the width of securement strip 36 is not coterminous with the width of absorbent pouch 30, rather, it is substantially narrower. In the preferred embodiment, the width of the securement strip 36 is finger-sized, or as displayed in FIG. 5, approximately ¼ the width of the absorbent pouch 30 and is positioned along the lengthwise center line of bottom layer 48 of absorbent pouch 30. Securement strip 36 is permanently bound to bottom layer 48 by employing similar techniques to those stated previously for assembling components of diaper 10.

In the preferred embodiment, fastening means 38 can be a coating of adhesive on the surface of securement strip 36 which is in facing relation to backsheet 14, and releasably joins absorbent pouch 30 to backsheet 14. Fastening means 38 extends along most of the length and width of the securement strip 36 surface which is in contact relation with backsheet 14. Fastening means 38 can be comprised of any adhesive or glue which is used in the art with a pressure sensitive adhesive being preferred. The adhesive strength is such that it is strong enough to attach absorbent pouch 30 and backsheet 14, yet releasable enough to allow the user to separate the absorbent pouch 30 from backsheet 14 after use. It is also preferable for the adhesive to be liquid impervious to ensure that the absorbent pouch 30 is not detached from backsheet 14 prematurely, after the wearer wets diaper 10. Nonlimiting examples of suitable adhesives are Century A-305-IV™ manufactured by Century Adhesives Corporation and Instant Lok 34-2823™ manufactured by National Starch Company.

Gripping tab 34 is shown as an integral extension of securement strip 36. Therefore, in the preferred embodiment, gripping tab 34 and securement strip 36 are made using the same material. Gripping tab 34 extends past the length of absorbent pouch 30. The length of the gripping tab 34 is of sufficient size to allow the user to grip and pull absorbent pouch 30 out through opening 32 with the optimal level of ease and convenience to the user. Gripping tab 34 is also utilized to permanently secure absorbent pouch 30 into its final rolled position before discarding, by fastening to securement strip 36. In the preferred embodiment, the width of gripping tab 34 is the same as the width of securement strip 36 and the shape of gripping tab 34 is square; although, it is readily apparent that gripping tab 34 can be constructed utilizing other sizes, shapes and materials.

FIG. 5A shows a portion of absorbent pouch 30 and securement strip 36 where gripping tab 34 is located. Gripping tab 34 is shown having a tab adhesive 56 and a release liner 58. The tab adhesive 56 is a coating of pressure sensitive adhesive applied to the surface of gripping tab 34. Tab adhesive 56 can be comprised of the same adhesive used for fastening means 38 or of any other pressure sensitive adhesive that is used in the art for such purposes. It is also preferable for tab adhesive 56 to be liquid impervious. Tab adhesive 56 and release liner 58 are located on the surface of gripping tab 34 that is in facing relation with absorbent pouch 30. For added fastening reinforcement, tab adhesive 56 is used to permanently secure gripping tab 34 to securement strip 36 in order to lock absorbent pouch 30 into its final rolled position before discarding. Absorbent pouch 30 can also be secured into its final position by joining gripping tab 34 with fastening means 38, without using tab adhesive 56. Therefore, tab adhesive 56 and release liner 58 can be omitted, but it is preferable to include tab adhesive 56 to ensure that absorbent pouch 30 remains in its rolled position after discarding. Release liner 58 completely covers tab adhesive 56 to prevent the adhesive from sticking to extraneous surfaces, drying, or getting wet inside the diaper 10, prior to the user peeling it from the surface of tab adhesive 56. Any commercially available release liner commonly used in the art can be utilized herein, although it is preferable that release liner 58 is made of liquid impermeable material.

FIG. 5B shows a preferred embodiment of gripping tab 34. FIG. 5B includes all the elements previously described for FIG. 5A, with the exception of the type of release liner 58 used. In this embodiment, release liner 58 is shown as an integral extension of securement strip 36 and gripping tab 34. Therefore, in the preferred embodiment, release liner 58, gripping tab 34 and securement strip 36 are all manufactured using the same material. Release liner 58 extends passed the length of gripping tab 34. The length and width dimensions of release liner 58 are the same as those used for gripping tab 34; although, it is readily apparent that release liner 58 can be constructed utilizing other shapes and dimensions.

Figure 6:
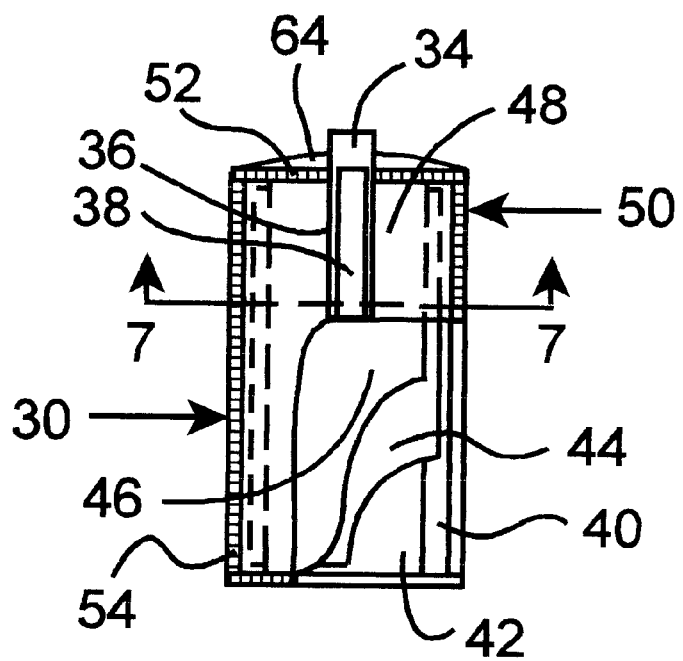
FIG. 6 representatively shows a top plan view of the absorbent pouch embodiment having portions cut away to reveal the underlying structure.
Figure 7:
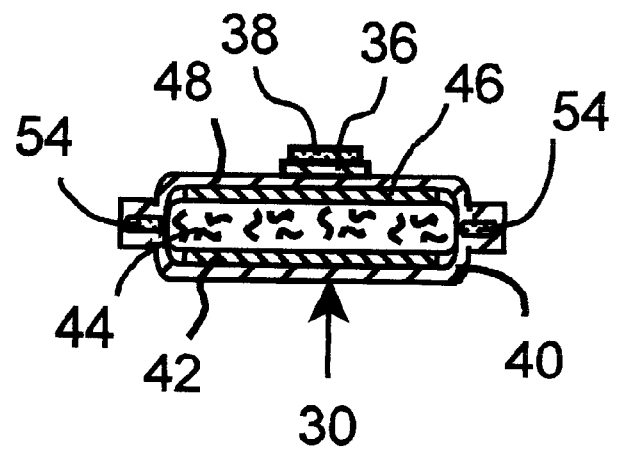
FIG. 7 representatively shows a cross-sectional view of the absorbent pouch taken along line 7—7 of FIG. 6 of the present invention.

With reference to the embodiment of the invention, representatively shown in FIGS. 6 and 7, absorbent pouch 30 is constructed of a liquid permeable top layer 40, a top tissue layer 42, an absorbent body 44, a bottom tissue layer 46, and a liquid permeable bottom layer 48. Top and bottom tissue layers 42 and 46 are superposed in facing relation with top and bottom layers 40 and 48. The absorbent body 44 is sandwiched between the top and bottom tissue layers 42 and 46. Top and bottom layers 40 and 48 completely encase top tissue layer 42 absorbent body 44 and bottom tissue layer 46 to form the absorbent pouch 30. It is readily apparent that top and bottom layers 40 and 48 can also be manufactured as a single integral surface that wraps around to encase the entire absorbent contents of absorbent pouch 30. In such an embodiment, lengthwise binding 54 joins top and bottom layers 40 and 48 along the lengthwise edge of bottom layer 48. In the preferred embodiment, the shape of the absorbent pouch 30 is a rectangular plan form 50; although, it is readily apparent that other shapes, such as I-shape, or T-shape could also be utilized. It is preferable that the liquid permeable material of absorbent pouch 30 is flushable and biodegradable.

FIG. 6 shows top and bottom bindings 52 and lengthwise binding 54 joining top layer 40 and bottom layer 48. Therefore, the entire periphery of absorbent pouch 30 is bound by top and bottom bindings 52, and by two lengthwise bindings 54. Top and bottom bindings 52 and lengthwise bindings 54 releasably enclose the absorbent contents of absorbent pouch 30, which comprises top layer 40, top tissue layer 42, absorbent body 44, bottom tissue layer 46, and bottom layer 48. In the illustrated embodiment, peeling tabs 64 are shown along the entire top edge of absorbent pouch 30. It is readily apparent that peeling tabs 64 may be located along both top and bottom edges, or omitted altogether. The securement strip 36, partially shown, is centered along the entire length of the absorbent pouch 30 on the outer surface of bottom layer 48. The gripping tab 34 is shown surpassing the length of the absorbent pouch 30 along the lengthwise center line.

FIG. 7 is a cross sectional view of FIG. 6 taken along line 7—7 of absorbent pouch 30. Top and bottom layers 40 and 48 are shown as separate surfaces where the top layer 40 is represented by the face positioned in contact relation to topsheet 12, and bottom layer 48 is represented by the face positioned in contact relation to backsheet 14. Two lengthwise bindings 54 releasably join the superposed top and bottom layers 40 and 48 along the lengthwise edges of absorbent pouch 30. In this embodiment, the securement strip 36 is located on the outer surface of bottom layer 48 and is contact relation to backsheet 14. Fastening means 38 is shown on the outer surface of securement strip 36.

Such layers of absorbent pouch 30 can be joined together employing similar techniques to those stated previously for assembling components of diaper 10. Alternatively, the components can be attached with adhesives, such as hot melt pressure-sensitive adhesives, or by spraying droplets or filaments of adhesive along the inner layers of absorbent pouch 30. Top and bottom and lengthwise bindings 52 and 54 can be formed by any using peelable bond known in the art, such as ultrasonic bonds, adhesive bonds, or other suitable releasable bonds. The purpose of top and bottom and lengthwise bindings 52 and 54 on absorbent pouch 30 is to releasably unite the various elements of the absorbent pouch 30 into a whole.

Absorbent pouch 30 may be manufactured in a wide variety of sizes with variations in dimensions and configurations. In the preferred embodiment the shape of absorbent pouch 30 is rectangular 50 with a convex peeling tab 64 extending out past the top edge. It is readily apparent that absorbent pouch 30 may be manufactured in a wide variety of sizes and shapes; for example, hourglass, I-shape, or T-shape, and can be utilized with various dimensions and configurations. The length and width dimensions of absorbent pouch 30 are dictated by the size of the diaper 10. The total absorbent capacity and size of the absorbent pouch 30 can be varied to accommodate wearers ranging from infants through adults. Furthermore, the total absorbent capacity of the absorbent pouch 30 should be compatible with the design exudate loading in the intended use of the diaper 10.

Peeling tabs 64 are used to help the user peel apart top and bottom and lengthwise bindings 52 and 54 in order to expose the absorbent contents of absorbent pouch 30. Peeling tabs 64 are finger-sized and have a rounded shape that extends along the entire top edge of absorbent pouch 30. It is readily apparent that peeling tabs 64 may be manufactured in a wide variety of sizes with variations in dimensions and configurations. Peeling tabs 64 are an integral extension of top and bottom layers 40 and 48. Therefore, in the preferred embodiment, peeling tabs 64, top layer 40 and bottom layer 48 are all manufactured using the same material.

The top and bottom layers 40 and 48 are fabricated out of any liquid permeable material suitable for absorbing, containing and restraining contents of absorbent pouch 30. The same materials utilized for topsheet 12 may also be used for top and bottom layers 40 and 48. It is preferable that the top and bottom layers 40 and 48 are constructed of hydrophobic material in order to lock wetness within the absorbent pouch 30. Preferably, flushable material is used to manufacture top and bottom layers 40 and 48. Furthermore, biodegradable flushable material which is susceptible to breakdown over a relatively short period of time, when exposed to natural elements such as air, heat and moisture, can be used to accelerate the degrading process once discarded. The size, shape and dimensions of top and bottom layers 40 and 48 are dictated by those of the absorbent pouch 30.

The top and bottom tissue layers 42 and 46 improve the tensile strength of the absorbent body 44 and reduce the tendency for it to split, lump or ball when wetted. Top and bottom tissue layers 42 and 46 also help to improve lateral wicking of the absorbed exudates, thereby providing a more even distribution of absorbed human exudates throughout the absorbent body 44 of absorbent pouch 30. The tissue layers comprise an absorbent cellulosic material, such as creped wadding or a high wet-strength tissue. While tissue layers are preferably rectangular 50 and coterminous with top and bottom layers 40 and 48, they may have different dimensions, shape, configuration, or they may be omitted entirely.

The absorbent body 44 may be composed of any means which is generally compressible, comfortable, non-irritating to the wearer's skin, and capable of absorbing and retaining liquids and certain body exudates. In the preferred embodiment, the shape of absorbent body 44 is rectangular 50 and the dimensions of length and width are slightly smaller than those of absorbent pouch 30. The total absorbent capacity and size of the absorbent body 44 is dictated by the absorbency requirements of diaper 10 and can be varied to accommodate wearers ranging from infants through adults. Furthermore, the total absorbent capacity of the absorbent body 44 should be compatible with the design exudate loading in the intended use of the diaper 10. The absorbent body 44 may be manufactured from a wide variety of materials commonly used in disposable diapers and other absorbent articles, such as comminuted wood pulp which is generally referred to as airlift. Nonlimiting examples of suitable absorbent materials such as those known in the art may include creped cellulose wadding, super absorbent polymers, absorbent gelling materials, or any equivalent materials or combination of materials. It is preferable that absorbent body 44 is made of biodegradable and flushable material.

OPERATION OF THE INVENTION

The following description shows the operation of the invention. As will be realized, the invention is capable of some operational variations, and its several details are capable of modifications in various obvious respects, all without departing from the invention. Accordingly, the following operational descriptions are to be regarded as illustrative in nature, and not as restrictive. Variations in the operation and utilization of the invention are applicable, and the following are only examples and not limitations.

Figure 8:
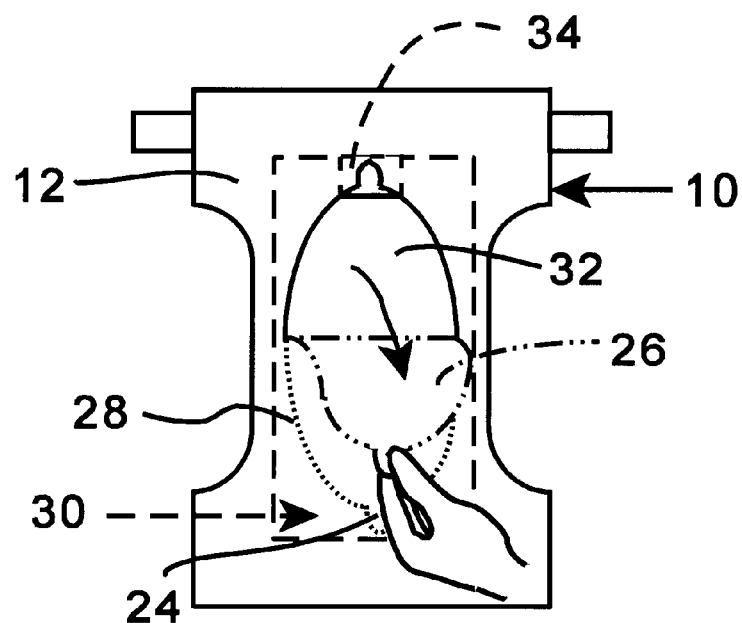
FIG. 8 representatively shows a perspective view of the absorbent article having moving parts to illustrate the functionality of the present invention.

Once diaper 10 has been used, the novel elements of the present invention are shown by separating various components of diaper 10, which can be discarded individually. The embodiment of FIG. 8 illustrates the operation of removing the detachable liner 26 of the present invention. The detachable liner 26 is removed by utilizing pulling tab 24 and detaching means 28 to tear detachable liner 26 off the surface of topsheet 12. This process is initiated by taking hold of pulling tabs 24, located on the top and bottom peaks of the detachable liner 26, and pulling away from diaper 10 towards the center of diaper 10. This pulling action continues along the entire periphery of detaching means 28 until the detachable liner 26 has been completely extracted from the surface of topsheet 12. Consequently, an opening 32 is created on the surface of topsheet 12, after detachable liner 26 has been completely removed.

Figure 9:
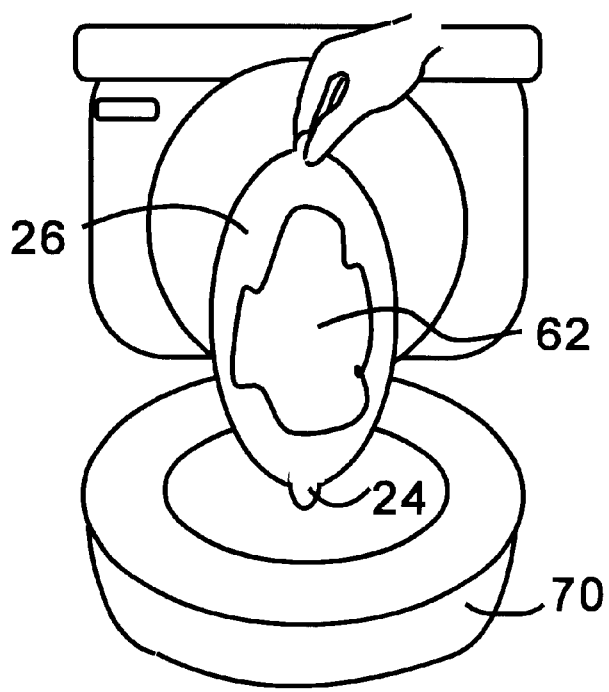
FIG. 9 representatively shows a perspective view of the detachable liner and solid body waste prior to discarding.

FIG. 9 shows the detachable liner 26, containing solid waste 62 on its surface, after it has been used and separated from diaper 10. After the detachable liner 26 is removed from the absorbent article, the liner can be flushed down the toilet 70 along with any accompanying body exudates, and can be treated by the sewage system.

Figure 10:
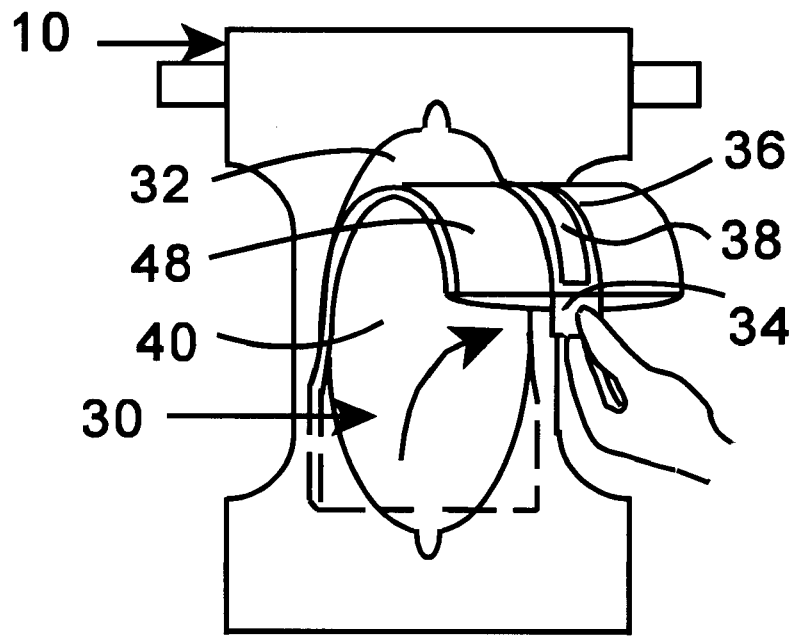
FIG. 10 representatively shows a perspective view of the absorbent article having moving parts to illustrate the functionality of the present invention.

The embodiment shown on FIG. 10 illustrates the utilization of opening 32, created on the surface of topsheet 12, to release the absorbent pouch 30 from the confines of the diaper 10. The absorbent pouch 30 is releasably secured to the backsheet 14 by a securement strip 36 and a fastening means 38 until it is extracted out of opening 32. Absorbent pouch 30 is removed from the interior of diaper 10, by taking hold of gripping tab 34 and pulling until the entire absorbent pouch 30 has been completely extracted from diaper 10 through opening 32.

Figure 11:
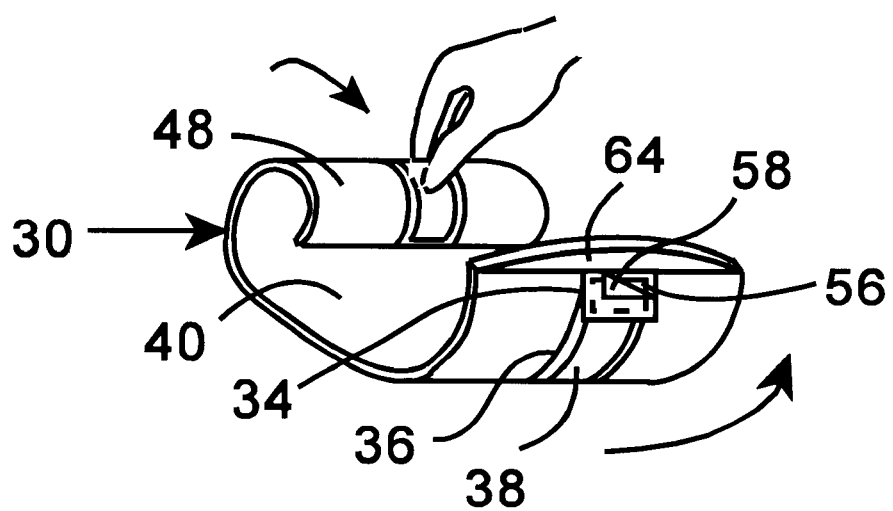
FIG. 11 representatively shows a perspective view of the final rolling operation of the absorbent pouch prior to discarding.

FIG. 11 shows a method of preparing absorbent pouch 30 for disposal, after it has been released from the interior of diaper 10. To prevent direct contact by the user's fingers with the absorbent pouch 30, gripping tab 34 and securement strip 36 can be utilized by the user to handle and roll the absorbent pouch 30 into its final position. Absorbent pouch 30 is rolled starting from the end opposite the gripping tab 34 with the securement strip 36 facing outward. The rolling of absorbent pouch 30 continues until the end containing gripping tab 34 is reached. Once the absorbent pouch 30 is in position, release liner 58 is removed from gripping tab 34 to expose tab adhesive 56.

Figure 12:
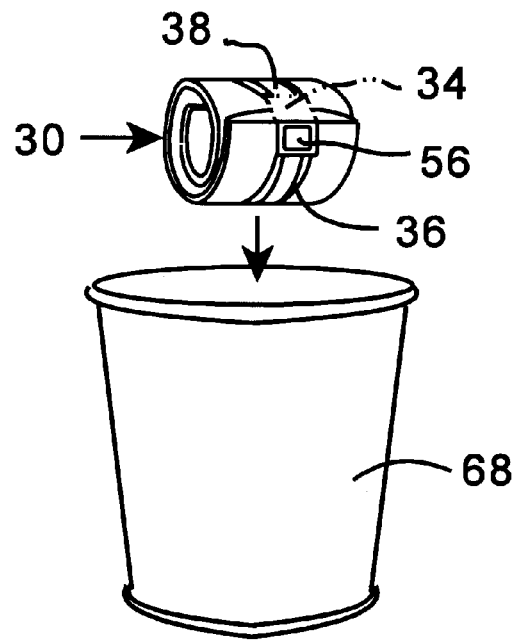
FIG. 12 representatively shows a perspective view of the securement operation of the rolled absorbent pouch prior to discarding.

FIG. 12 shows how the absorbent pouch 30 is rolled and permanently secured into its final position by joining tab adhesive 56 with fastening means 38, prior to being discarded. After the absorbent pouch 30 has been prepared for discarding, it can be disposed of separately from the remnants of the diaper 10. The absorbent pouch 30 now has a higher potential for degrading because it is no longer attached to the backsheet 14 that inhibits decomposition of the article after being thrown away.

Figure 13:
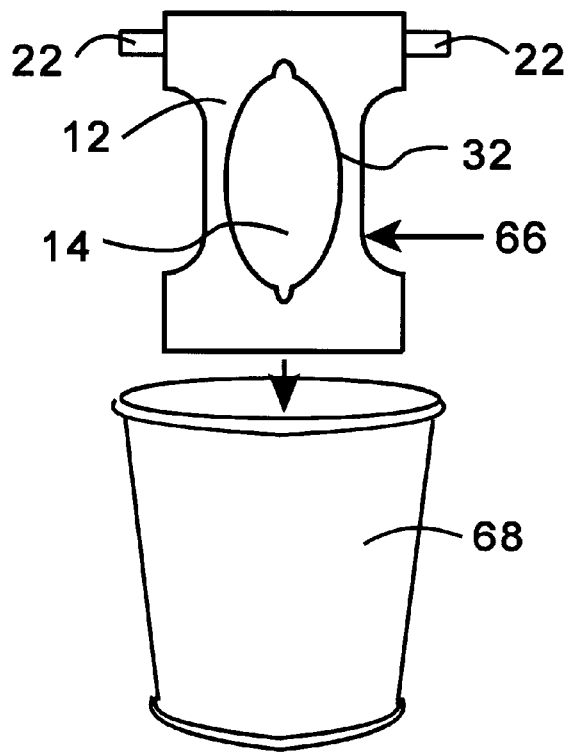
FIG. 13 representatively shows a perspective view of the remainder of the absorbent article of the invention prior to discarding.

FIG. 13 shows the remnants of diaper 10 after both the detachable liner 26 and absorbent pouch 30 have been removed. All that remains is a hollow containment pocket 66 consisting of a topsheet 12 and a backsheet 14 which are permanently bound together in facing relation. Topsheet 12 also includes the opening 32 that was created previously.

The preferred method of discarding the remaining containment pocket 66 (not shown) of diaper 10 is to roll it with the backsheet 14 facing outward, and then securing it with fastening members 22 into its final position. Once diaper 10 has been secured in this final position, it can be disposed of in a waste receptacle 68.

Figure 14:
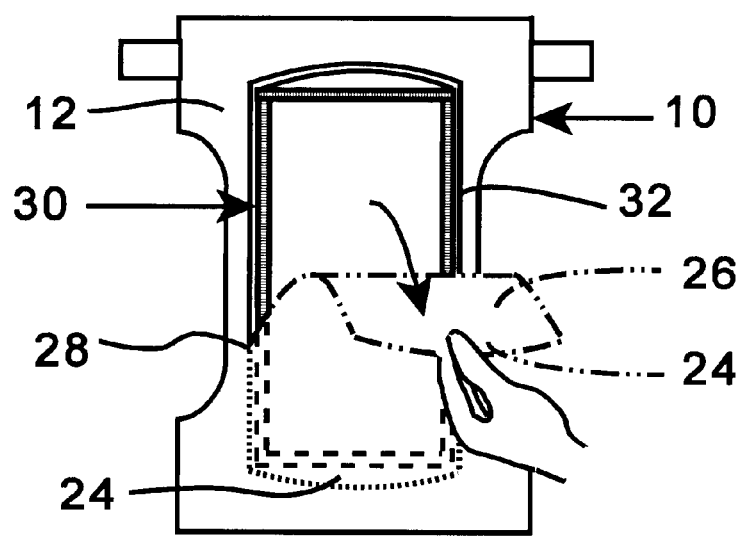
FIG. 14 representatively shows a perspective view of the absorbent article having moving parts to illustrate the functionality of the present invention.

FIG. 14 illustrates a preferred design for the detaching means 28, detachable liner 26, and pulling tabs 24. In this embodiment detaching means 28 encompasses a much larger portion of topsheet 12 than previously illustrated. The shape of detachable liner 26 is generally rectangular. Pulling tabs 24 are convex and extend along the entire top and bottom edges of detachable liner 26. In this embodiment, detachable liner 26 and pulling tabs 24 are integral and are manufactured from the same material. The operation is the same as stated in FIG. 8 above.

Figure 15:
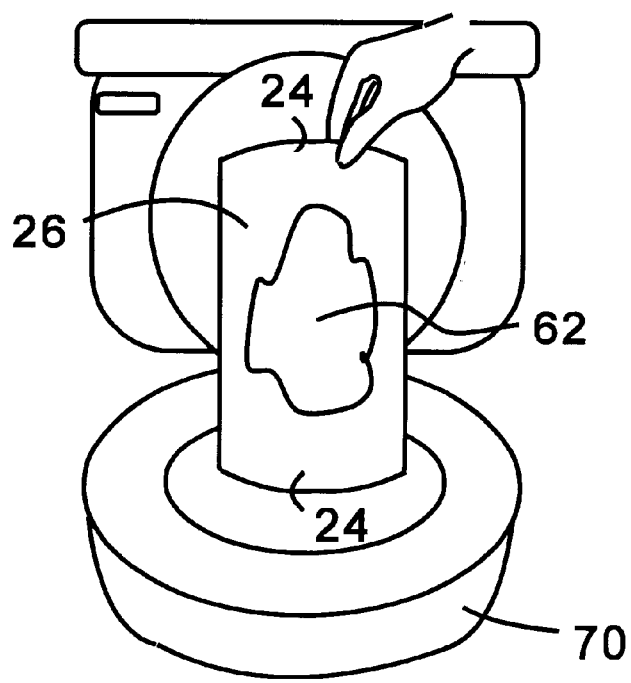
FIG. 15 representatively shows a perspective view of the detachable liner and solid body waste prior to discarding.

FIG. 15 shows the detachable liner 26, containing solid waste 62 on its surface, after it has been used and separated from diaper 10. After the detachable liner 26 is detached from the absorbent article, it can be flushed down the toilet 70 along with any accompanying body exudates, and can be treated by the sewage system.

Figure 16:
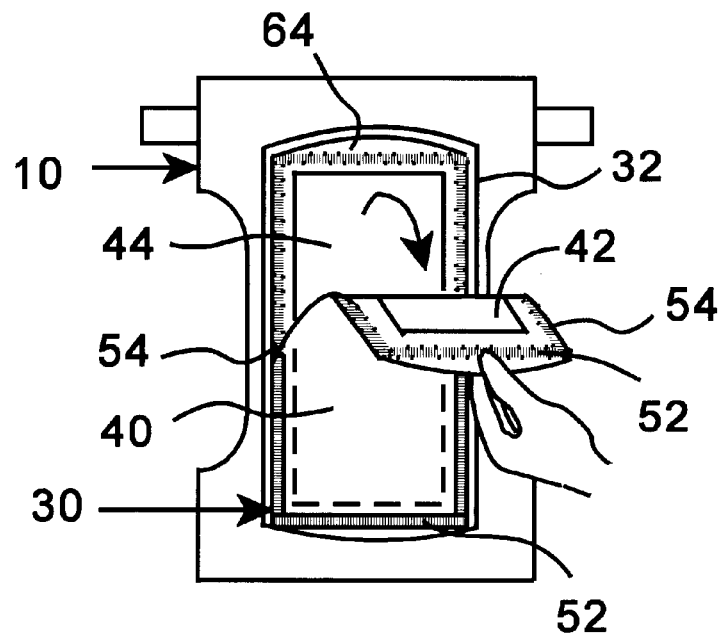
FIG. 16 representatively shows a perspective view of the absorbent article having moving parts to illustrate the functionality of the present invention.

FIG. 16 illustrates the preferred method of discarding the absorbent contents of diaper 10. After the detachable liner 26 has been remove to create opening 32, the absorbent pouch 30 is exposed. Top layer 40 is separated from absorbent pouch 30 by gripping on peeling tab 64 and pulling away from the article until top layer 40 is detached, thus, exposing the absorbent contents of absorbent pouch 30. The present invention allows for top layer 40 to be partially or entirely separated from absorbent pouch 30, to accommodate the preference of the user.

Figure 17:
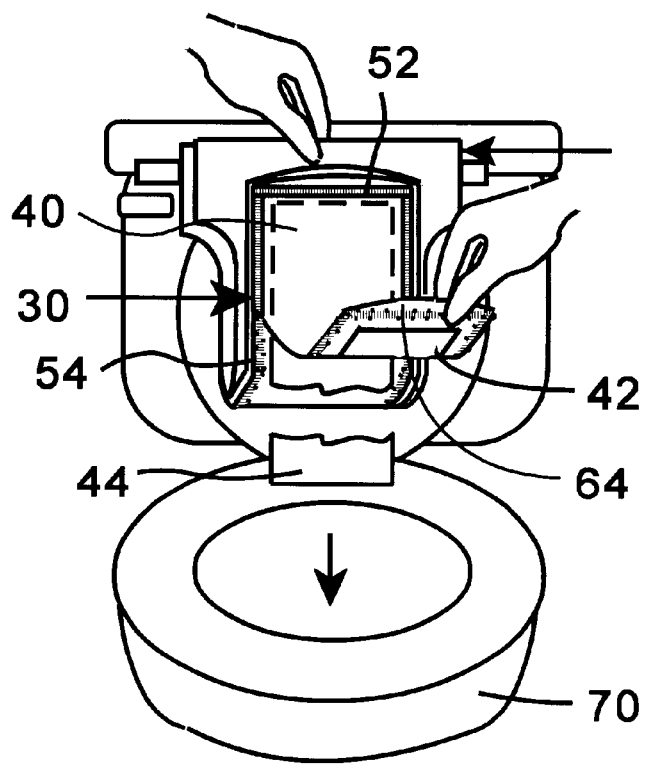
FIG. 17 representatively shows a perspective view of the absorbent article having moving parts to illustrate the functionality of the disposal of the present invention.

FIG. 17 shows the contents of the absorbent pouch 30 being flushed down the toilet 70. The user holds the diaper 10 with one hand and holds the top layer 40 out with the other hand to open absorbent pouch 30 in order to let the absorbent contents drop into the toilet 70. The entire contents can be dropped to be disposed of in a single flush, or in segments and subsequently flushed after each dropping. This conveniently allows the user the option to flush the absorbent contents based on the flushing capacity of the toilet 70, and also allows for flushing in segments the contents of larger diapers or adult incontinence briefs without the risk of clogging the toilet 70. In the present invention absorbent pouch 30, as a whole, is not intended to be flushed. Rather, absorbent pouch 30 is designed to be separated and only those components designed to be flushed are disposed into the toilet 70 and the other components are disposed of as described in FIG. 13 with the remainder of diaper 10. Bottom layer 48 is not flushed, and instead remains attached to diaper 10 via securement strip 36 and fastening implement 38. Top layer 40 is designed to be entirely detached from absorbent pouch 30 and flushed, or to be partially removed to remain on the article along with the bottom layer 48, and with the remnants of diaper 10.

Figure 18:
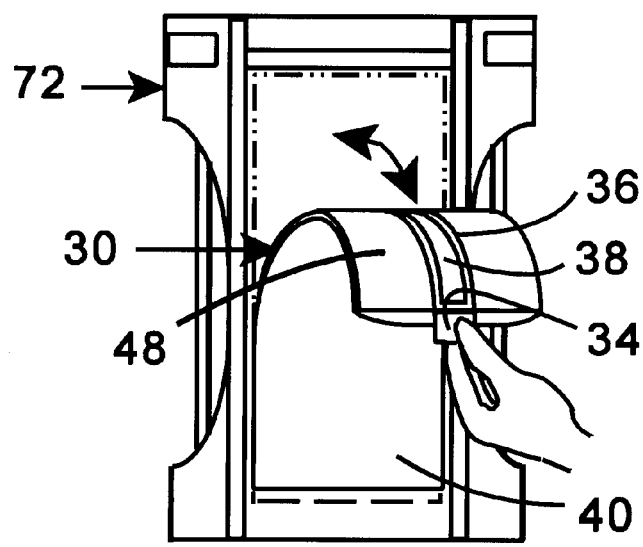
FIG. 18 representatively shows a perspective view of an alternative application of the absorbent article having moving parts to illustrate the improvements of the present invention.

FIG. 18 shows an alternative application of the absorbent pouch 30. In this embodiment, the absorbent pouch 30 is used alone, independent of the hollow containment pocket 66 and the detachable liner 26, and is fastened to a reusable diaper cover 72, although, it is readily apparent that training pants, or other reusable undergarments may also be used. Diaper cover 72 is not part of the present invention. This embodiment illustrates the versatility of the present invention, by the utilization of the absorbent pouch 30 by itself for the absorption of body waste. The disposal of the absorbent pouch 30 is performed the same way as described above. In this illustration, the absorbent pouch 30 is removed from the diaper cover 72, and can be rolled as described in FIGS. 11 and 12.

Figure 19:
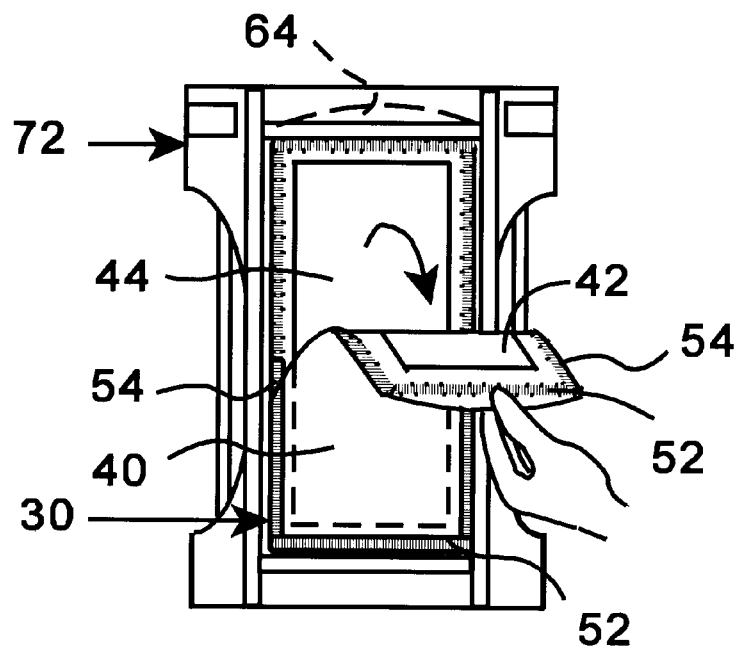
FIG. 19 representatively shows a perspective view of an alternative application of the absorbent article having moving parts to illustrate the improvements of the present invention.

FIG. 19 shows the other method for disposing of the absorbent pouch 30 when used alone, as described in FIG. 17, above. In this illustration, the outer layers are detached using peeling tabs 64, then the absorbent contents are released into toilet 70 (not shown). In this embodiment, bottom layer 48 and securement strip 36, do not remain on the reusable article, but are instead disposed of in a waste receptacle (not shown).

CONCLUSIONS AND RAMIFICATIONS

The reader will see that the detachable structure of the absorbent article of the invention provides more suitable alternatives to discard various components of disposable absorbent articles individually. The improved design is potentially advantageous to the preservation of the ecology by providing solutions to the environmental problems that have been associated with contemporary absorbent articles. The present invention provides a detachable liner 26 that may be removed from the article and flushed down the sewage system along with most of the solid waste material contained on the absorbent article. Pulling tabs 24 are provided to grip onto and pull the detachable liner 26 to extract it off the topsheet 12 of the article. The absorbent pouch 30 releasably encloses the absorbent contents of the article located between the topsheet 12 and backsheet 14 of the hollow containment pocket 66. The securement strip 36 and fastening means 38 are used to releasably join the absorbent pouch 30 within the basic framework of the hollow containment pocket 66 to secure the absorbent pouch 30 into position and prevent it from shifting or moving out of place in the article. The opening, created on the surface of topsheet 12 after removing the detachable liner 26, provides an exiting means to release the contents of diaper 10 and allows for the pouch to be discarded separately from the article. The gripping tab 34 is used to pull the absorbent pouch 30 out of the absorbent article through the opening 32 and is also used to permanently secure the absorbent pouch 30 into its final, rolled position prior to discarding, by fastening gripping tab 34 to the fastening means 38 on the securement strip 36. Securement Strip 36 and fastening means 38 are also used to handle the absorbent pouch 30 after use to prevent the user from touching the wet surface of the pouch 30, while preparing it for disposal into its final rolled position. The absorbent pouch 30, which contains the majority of the diaper's absorbent material, has a higher potential for biodegrading now because it is no longer attached to the backsheet 14, which inhibits decomposition of the article after being thrown away. The invention offers the user an alternative disposal option by allowing for the detachment of the absorbent pouch 30 binding by pulling the peeling tabs 64 apart in order to open the pouch 30 and allow the absorbent contents to fall by gravity into the toilet 70 to be flushed. The absorbent pouch 30 is not intended to flushed as a whole. Therefore, depending on the size of the diaper 10 and the flushing capacity of the toilet 70, the user may flush the contents of the absorbent pouch 30 in segments to reduce the risk of clogging the toilet 70. An alternative application of the absorbent pouch 30 reveals the versatility of the present invention, by the autonomous utilization of the absorbent pouch 30 for the absorption of body waste. The absorbent pouch 30 may be used alone, independent of the hollow containment pocket 66 and the detachable liner 26, and may be fastened to reusable undergarments, diaper covers, training pants, or other similar reusable garments.

Therefore, the absorbent pouch 30 is not restricted for use with disposable absorbent articles, but may also be used in conjunction with reusable absorbent articles or reusable undergarments. The autonomous use of the absorbent pouch 30 is applicable for use with feminine care pads as well. Therefore, the diversity of the article of the present invention allows for utilization with a broad spectrum of disposable hygienic products with various disposal applications that are beneficial to the environment.

While the above description contains many specificities, these should not be construed as limitations on the scope of the invention, but rather as an exemplification of the preferred embodiments thereof. Many other variations are possible and have been delineated in the above description. For example, the shape and size of the detaching means 28 may vary to provide the greatest ease and convenience for the removal of the detachable liner 26, and to accommodate the largest surface area of the detachable liner 26 for containing body waste, such as rectangular, elliptical, or rectangular with rounded edges. Pulling Tabs 24 may vary in size and shape, such as convex, parabolic, triangular, or rectangular. The variations for the location of pulling tabs 24 on the detachable liner 26 include: the central upper peak, the central lower peak, both upper and lower peaks, or they may be omitted altogether. The detachable liner 26 and pulling tabs 24 may be manufactured as an integral extension of the topsheet 12, or from completely different material. The size and shape of the absorbent pouch 30 may also vary to accommodate the total absorbent capacity of the pouch 30 and should be compatible with the design exudate loading in the intended use of the absorbent article; for example, rectangular, hourglass, I-shape, or T-shape, and can be utilized with various dimensions and configurations. Although the topsheet 12, detachable liner 26, and outer layer of the absorbent pouch 30 may be manufactured from the same liquid permeable, flushable, and biodegradable material, they may also be manufactured from different materials that still meet the above criteria. The size and shape of the peeling tabs 64 may vary, such as rounded, parabolic, or rectangular, and may be located on the top edge, bottom edge, or both top and bottom edges of absorbent pouch 30. Peeling Tabs 64 may be manufactured as integral extensions of the outer layers of the absorbent pouch 30, same material but not integral extensions, or from a different material altogether. Gripping tab 34 may be an integral extension of securement strip 36 or manufactured from a different material, and may be located on the absorbent pouch 30 extending from the top edge, bottom edge, or both top and bottom edges. The tab adhesive 56 may be manufactured from a the same adhesive used for fastening means 38, a different adhesive, or may be omitted along with release liner 58. The release liner 58 may be manufactured as an integral extension of gripping tab 34 and securement strip 36, or from different material. Although it is preferable for the widths of securement strip 36, gripping tab 34, and release liner 58 to be the same, they may vary to provide the greatest convenience to the user and ease for their functional purposes.

It is obvious from the foregoing that the present invention encompasses the process of making a disposable absorbent article, where the process includes releasably attaching the absorbent pouch to the basic framework of the article, and covering the pouch with a liquid permeable detachable liner positioned to be in contact with the wearer and the pouch, and detachable from the framework.

Accordingly, the scope of the invention should be determined not by the embodiments illustrated, but by the appended claims and their legal equivalents.

I claim:

1. A liquid permeable absorbent pouch designed to be used in combination with an article for containing solid and liquid body wastes including a disposable diaper, reusable diaper, reusable diaper cover, training pants, feminine care pad, incontinence article, or similar article, and designed to be detached and disposed of independently from an article for containing solid and liquid body wastes along with body wastes deposited on and in the absorbent pouch, the absorbent pouch comprising:

(a) liquid permeable absorbent contents and an outer liquid permeable layer of the pouch encasing the absorbent contents of the pouch, and (b) a fastening means attached to the pouch and designed to be attached to an article for containing solid and liquid body wastes, whereby body wastes and associated smell can be readily removed and disposed of independently from an article for containing solid and liquid body wastes, and whereby the amount of material sent to a landfill is thereby reduced.

2. The absorbent pouch of claim 1, wherein said fastening means is designed to be severed and detached from the pouch, and wherein the pouch absorbent contents and pouch outer layer are flushable and biodegradable, whereby the pouch can be flushed after detaching said fastening means.

3. The absorbent pouch of claim 1, wherein said fastening means comprises a liquid impermeable adhesive attached to the pouch and designed to be releasably attached to an article for containing solid and liquid body wastes, whereby the adhesive releasably maintains the pouch in a stationary position, and prevents the pouch from moving, with respect to an article for containing solid and liquid body wastes.

4. The absorbent pouch of claim 3, further comprising a gripping tab on the pouch, for pulling the pouch away from an article for containing solid and liquid body wastes, wherein said liquid impermeable adhesive provides a dry area on the absorbent pouch for handling and rolling the pouch into a rolled position, and wherein said liquid impermeable adhesive is designed to secure the pouch in a rolled pouch position prior to disposal, whereby contact between a user's fingers and body waste is minimal when handling, rolling or securing the absorbent pouch.

5. The absorbent pouch of claim 1, further comprising a binding incorporated into the outer layer of the pouch to releasably encase the absorbent contents inside the pouch, whereby the absorbent pouch can be readily opened by severing the pouch outer layer along said binding, wherein the pouch absorbent contents are adapted to be disposed of separately from the pouch along with body wastes deposited on and in the pouch absorbent contents, and wherein the outer layer comprises outer liquid permeable top and bottom layers attached to each other along said binding, and whereby the top layer can be entirely detached by severing along said binding, and disposed of independently from the pouch.

6. The absorbent pouch of claim 5, further comprising a peeling tab attached to, or forming an integral part of the outer layer of, the pouch for pulling and opening the pouch outer liquid permeable layer along the pouch binding to readily release the absorbent contents inside the pouch, whereby the absorbent pouch can be readily opened by using the peeling tab to sever said binding.

7. The absorbent pouch of claim 1, further comprising a liquid permeable detachable liner attached to an article for containing solid and liquid body wastes and positioned over the absorbent pouch, wherein the detachable liner is adapted to be readily removed, along with body wastes deposited on the detachable liner, and disposed of separately from an article for containing solid and liquid body wastes and the pouch.

8. The absorbent pouch of claim 7, further comprising a detaching means along the detachable liner adapted for readily removing the liner from an article for containing solid and liquid body wastes, wherein said detaching means comprises a series of breakable perforations, whereby the detachable liner can be extracted from an article for containing solid and liquid body wastes by breaking the perforations, and further comprising a pulling tab attached to, or forming an integral part of, the detachable liner for pulling the detachable liner away from an article for containing solid and liquid body wastes, and wherein the detachable liner is flushable and biodegradable.

9. An absorbent article including a disposable diaper, reusable diaper, training pants, feminine care pad, incontinence brief or similar article for containing solid and liquid human body wastes, the article comprising:

(a) a liquid permeable detachable liner comprising a detachable portion of the article, wherein the detachable liner is adapted to be readily removed and disposed of separately from the article along with body wastes deposited on the liner, (b) a hollow containment pocket formed between the detachable liner and the article, (c) a liquid permeable absorbent pouch comprising outer liquid permeable top and bottom layers and liquid permeable absorbent contents, wherein the absorbent contents are adapted to be readily removed in portions from inside the absorbent pouch and flushed in segments to avoid clogging a toilet, wherein the pouch is positioned inside said hollow containment pocket and under the detachable liner, and wherein the absorbent pouch is adapted to be detached and disposed of separately from the article along with body wastes deposited on and in the absorbent pouch, (d) a fastening means for releasably attaching the absorbent pouch, within said hollow containment pocket, to the- absorbent article, wherein said fastening means is adapted to keep the pouch from moving with respect to the article, wherein said fastening means is non-flushable and is attached to the bottom layer of the absorbent pouch and prevents the entire pouch from being flushed as a whole and thereby prevents clogging a toilet, wherein said fastening means and the bottom layer are adapted to be severed from the pouch, wherein the pouch is adapted to be flushed after removing said fastening means and the bottom layer, and wherein all parts of the pouch are flushable and biodegradable except for said fastening means and the bottom layer of the pouch, and (e) a binding incorporated into the outer layers of the pouch adapted to readily release the absorbent contents from inside the pouch prior to disposal so that said absorbent contents can be disposed of separately from the pouch along with body wastes deposited in the pouch contents, whereby the absorbent pouch is adapted to be readily extracted from the article through an opening in said hollow containment pocket made by removing the detachable liner, whereby body wastes and associated smell are promptly removed by flushing in a toilet, and whereby the amount of material sent to a landfill is thereby reduced.

10. The article of claim 9, wherein said hollow containment pocket comprises a liquid permeable topsheet positioned over the absorbent pouch and joined in facing relation along its entire periphery to a liquid impermeable backsheet positioned under the absorbent pouch, wherein the absorbent pouch is encased within the interior of said hollow containment pocket, and wherein the pouch is releasably secured to the article by said fastening means.

11. The article of claim 9, further comprising a detaching means along the detachable liner adapted for readily removing the liner from the article, wherein said detaching means comprises a series of breakable perforations incorporated along the periphery of the detachable liner, whereby the detachable liner can be extracted from the article by breaking the perforations.

12. The article of claim 9, wherein said binding secures the outer top and bottom layers together along the periphery of the layers, wherein the absorbent contents are releasably encased between the top and bottom layers, wherein the absorbent pouch is adapted to be readily opened by severing said binding along one or more sides of the pouch outer layers, wherein the non-flushable fastening means is attached to the bottom layer, wherein the pouch is adapted to be flushed after removing said fastening means and the bottom layer, and wherein all the parts of the pouch are flushable and biodegradable except for the bottom layer and said fastening means.

13. The article of claim 9, wherein said fastening means comprises a liquid impermeable securement strip attached to the bottom layer of the pouch and a pressure sensitive adhesive that is impervious to liquid positioned along the securement strip on the surface opposite the bottom layer, whereby the adhesive along the securement strip releasably maintains the pouch within said hollow containment pocket in a stationary position, and prevents the pouch from moving, with respect to the article.

14. The article of claim 9, further comprising a peeling tab attached to the pouch for gripping and opening the pouch at the pouch binding to readily release the absorbent contents inside the pouch, whereby the absorbent pouch can be readily opened by using the peeling tab to sever said binding along one or more sides of the pouch outer layers.

15. The article of claim 9, further comprising a gripping tab attached to said fastening means, for pulling the pouch away from the article, wherein said fastening means provides a dry area on the absorbent pouch for handling and rolling the pouch into a rolled position, and wherein said fastening means secures the pouch in the rolled pouch position prior to disposal, whereby contact between a user's fingers and human waste is minimal.

16. The article of claim 9, further comprising a pulling tab attached to the detachable liner for pulling the detachable liner away from the article, and wherein the detachable liner material is flushable and biodegradable.

17. An absorbent article adapted for use in combination with a disposable diaper, reusable diaper, training pants, feminine care pad, incontinence brief or similar article for containing solid and liquid human body wastes, the article comprising:

(a) a liquid permeable absorbent pouch comprising outer liquid permeable top and bottom layers and liquid permeable absorbent contents, wherein the absorbent contents are adapted to be readily removed in portions from inside the absorbent pouch and flushed in segments to avoid clogging a toilet, wherein the absorbent pouch along with body wastes deposited on and in the pouch can be detached from a disposable diaper, reusable diaper, training pants, feminine care pad, incontinence brief or similar article and disposed of separately, (b) a fastening means for releasably attaching the absorbent pouch in a stationary position with respect to a disposable diaper, reusable diaper, training pants, feminine care pad, incontinence brief or similar article, wherein said fastening means is non-flushable and is attached to the bottom layer of the absorbent pouch and prevents the entire pouch from being flushed as a whole and thereby prevents clogging a toilet, wherein said fastening means and the bottom layer are adapted to be severed from the pouch, wherein the pouch is adapted to be flushed after removing said fastening means and the bottom layer, and wherein all parts of the pouch are flushable and biodegradable except for said fastening means and the bottom layer of the pouch, and (c) a binding incorporated into the outer layers of the pouch adapted to readily release the absorbent contents from inside the pouch prior to disposal so that said absorbent contents can be disposed of separately from the pouch along with body wastes deposited in the pouch contents, whereby body wastes and associated smell are promptly removed by flushing in a toilet, and whereby the amount of material sent to a landfill is thereby reduced.

18. The article of claim 17, wherein said binding secures the top and bottom layers together along the periphery of the layers, wherein the absorbent contents are releasably encased between the top and bottom layers, wherein the absorbent pouch is adapted to be readily opened by severing said binding along one or more sides of the pouch outer layers, wherein the non-flushable fastening means is attached to the bottom layer, wherein the pouch is adapted to be flushed after removing said fastening means and the bottom layer, and wherein all the parts of the pouch are flushable and biodegradable except for the bottom layer and said fastening means.

19. The article of claim 17, wherein said fastening means comprises a liquid impermeable securement strip attached to the bottom layer of the pouch and a pressure sensitive adhesive that is impervious to liquid positioned along the securement strip on the surface opposite the bottom layer, whereby the adhesive along the securement strip releasably maintains the pouch in a stationary position, and prevents the pouch from moving, with respect to a disposable diaper, reusable diaper, training pants, feminine care pad, incontinence brief or similar article.

20. The article of claim 17, further comprising a peeling tab attached to the pouch for gripping and opening the pouch at the pouch binding to readily release the absorbent contents inside the pouch, whereby the absorbent pouch can be readily opened by using the peeling tab to sever said binding along one or more sides of the pouch outer layers.

21. The article of claim 17, further comprising a gripping tab attached to said fastening means, for pulling the pouch away from the article, wherein said fastening means provides a dry area on the absorbent pouch for handling and rolling the pouch into a rolled position, and wherein said fastening means secures the pouch in the rolled pouch position prior to disposal, whereby contact between a user's fingers and human waste is minimal.

22. A liquid permeable absorbent pouch for containing solid and liquid body wastes, designed to be used in combination with a reusable article including a reusable undergarment, reusable diaper cover, reusable diaper, reusable training pants, or similar reusable article, and designed to be detached and disposed of independently from a reusable article along with body wastes deposited on and in the absorbent pouch, the absorbent pouch comprising (a) liquid permeable absorbent contents, an outer liquid permeable layer of the pouch encasing the pouch absorbent contents, and a binding along the outer layer of the pouch to enclose the pouch, and (b) a fastening means attached to the pouch and designed to be attached to a reusable article, whereby body wastes and associated smell can be readily removed and disposed of independently from the pouch and a reusable article, and whereby the amount of material sent to a landfill is thereby reduced.

23. The absorbent pouch of claim 22, wherein said fastening means comprises a liquid impermeable adhesive designed for releasably attaching the absorbent pouch in a stationary position with respect to a reusable article, and for preventing the pouch from moving with respect to a reusable article.

24. The absorbent pouch of claim 22, wherein said fastening means is designed to be severed and detached from the pouch, and wherein the pouch absorbent contents and pouch outer layer are flushable and biodegradable, whereby the pouch can be flushed after detaching said fastening means.

25. The absorbent pouch of claim 22, further comprising a peeling tab attached to, or forming an integral part of said outer liquid permeable layer of, the pouch for pulling and opening the pouch outer liquid permeable layer to readily release the absorbent contents inside the pouch.

26. An absorbent article for containing solid and liquid body wastes, comprising:

(a) a liquid permeable topsheet joined in facing relation along its periphery to a liquid impermeable backsheet, (b) a liquid permeable detachable liner comprising a detachable portion of the topsheet of the article, whereby the detachable liner is adapted to be readily removed and disposed of separately from the article along with body wastes deposited on the liner, (c) a liquid permeable absorbent pouch comprising liquid permeable absorbent contents and an outer liquid permeable layer of the pouch encasing the pouch absorbent contents, wherein the absorbent pouch is positioned between the topsheet and backsheet, and (d) a fastening means attached to the pouch and designed to be attached to the article, whereby body wastes and associated smell can be readily removed and disposed of independently from the article, and whereby the amount of material sent to a landfill is thereby reduced.

27. The article of claim 26, further comprising a detaching means adapted for readily removing the liner from the article, wherein said detaching means comprises a series of breakable perforations in the topsheet, and wherein the detachable liner is flushable and biodegradable, whereby the detachable liner can be extracted from the article by breaking the perforations, and whereby the absorbent pouch is adapted to be readily extracted from the article through an opening made in the topsheet from removing the detachable liner.

28. The article of claim 26, further comprising a peeling tab attached to, or forming an integral part of the outer layer of, the pouch for pulling and opening the pouch outer liquid permeable layer to readily release the absorbent contents inside the pouch.

29. The article of claim 26, further comprising a binding along the outer layer of the pouch to enclose the pouch, wherein the outer layer comprises outer liquid permeable top and bottom layers attached to each other along said binding, whereby the absorbent pouch can be readily opened by severing along said binding, whereby the absorbent contents are adapted to be readily removed from inside the absorbent pouch and disposed of separately from the article and the absorbent pouch along with body wastes deposited on and in the absorbent contents, and whereby the top layer can be entirely detached and disposed of independently from the pouch.

30. The article of claim 26, wherein said fastening means comprises a liquid impermeable adhesive attached to the pouch and designed to be releasably attached to the backsheet of the article, whereby the adhesive releasably maintains the pouch in a stationary position, and prevents the pouch from moving, with respect to the article.

31. The article of claim 26, wherein said fastening means is designed to be severed and detached from the pouch, and wherein the pouch absorbent contents and pouch outer layer are flushable and biodegradable, whereby the pouch can be flushed after detaching said fastening means.

\* \* \* \* \*

UNITED STATES PATENT AND TRADEMARK OFFICE
CERTIFICATE OF CORRECTION

PATENT NO. : 6,623,466 B1
DATED : September 23, 2003
INVENTOR(S) : Irene Richardson It is certified that error appears in the above-identified patent and that said Letters Patent is hereby corrected as shown below:

Column 19,
Line 41, delete "-" after "the".

Column 21,
Line 67, insert -- : -- after "comprising".

Signed and Sealed this

Fourth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,623,466 B1
DATED : September 23, 2003
INVENTOR(S) : Irene Richardson It is certified that error appears in the above-identified patent and that said Letters Patent is hereby corrected as shown below:

Column 7,
Line 45, after "permeable" insert -- substantially --.

Column 13,
Line 19, before "hydrophobic" insert -- substantially --.
Line 36, delete "creped wadding or".
Line 57, "airlift" should read -- airlaid --.

Column 14,
Line 9, "shown" should read -- demonstrated --.

Column 19,
Line 41, delete "-" after "the".

Column 21,
Line 67, insert -- : -- after "comprising".

This certificate supersedes Certificate of Correction issued May 4, 2004.

Signed and Sealed this

Twenty-ninth Day of March, 2005

JON W. DUDAS
*Director of the United States Patent and Trademark Office*